United States Patent [19]
Ayorinde et al.

[11] Patent Number: 5,498,733
[45] Date of Patent: Mar. 12, 1996

[54] SYNTHESIS OF NYLON-11 MONOMER

[75] Inventors: Folahan O. Ayorinde, Kettering; Chukwuma P. Nwaonicha, Adelphi, both of Md.

[73] Assignee: Howard University, Washington, D.C.

[21] Appl. No.: 93,029

[22] Filed: Jul. 19, 1993

[51] Int. Cl.⁶ .................. C11B 1/00; C11C 1/02
[52] U.S. Cl. ........... 554/132; 554/154; 554/160; 554/162; 554/213
[58] Field of Search ................. 554/132, 154, 554/160, 162, 213

[56] References Cited

FOREIGN PATENT DOCUMENTS 1283796  8/1972  United Kingdom .

OTHER PUBLICATIONS

Journal of American Chemical Society, vol. 83, 20 Apr. 1961, Lamar Field et al.: *Isomerization of Aldoximes to Amides under Substantially Neutral Conditions;* (Beckmann Rearrangement), pp. 1983–1986.

Contribution from the Department of Chemistry, Duke University, Nov. 1955, David S. Hoffenberg and Charles R. Hauser: *Dehydration or Beckmann Rearrangement of Aldoximes with Boron Fluoride. Conversion of Aldoximes to Corresponding Amides,* pp. 1496–1500.

Recueil, Journal of the Royal Netherlands Chemical Society, 95/5, May 1976, A. J. Leusink, et al.: *Beckmann rearrangement of aldoximes catalyzed by transition metal salts: a dehydration–hydration reaction,* pp. 123–125.

Department of Chemistry, University of California, Riverside, CA, Apr. 1974, Philip Radlick and Lauren R. Brown: *A Versatile Modification of the Hofmann Rearrangement,* p. 87.

Communications, p. 291, Apr. 1974: *Hofmann Rearrangement with Methyl Hupobromite in situ.*

Bulletin of the Chemical Society of Japan, vol. 46, No. 11, pp. 3474–3477 (1973), Mutsuo Kataoka and Masaji Ohno: *Syntheses and the Beckmann Fission of Cyclic α–Hydroxyimino Ketones.*

Primary Examiner—José G. Dees
Assistant Examiner—Dwayne C. Jones
Attorney, Agent, or Firm—Kenyon & Kenyon

[57] ABSTRACT

Nylon-11 monomer, 11-aminoundecanoic acid, is synthesized from 12-oxododecanoic acid oxime in a three-step reaction sequence which involves a Beckmann rearrangement, Hofmann degradation and hydrolysis. The aldoxime acid is hydrolyzed in the presence of nickel acetate tetrahydrate to give 11-carbamoylundecanoic acid. This amide is then treated with a solution of sodium methoxide and bromine at 70°–80° C. to give 11-(methoxycarbonylamino)undecanoic acid, which upon basic hydrolysis and subsequent neutralization, yields the 11-aminoundecanoic acid.

4 Claims, 11 Drawing Sheets

SYNTHESIS OF NYLON-11 MONOMER

FIELD OF THE INVENTION

This invention relates to 11-aminoundecanoic acid, the Nylon-11 monomer. More specifically, this invention relates to a process by which 12-oxododecanoic acid oxime which is derived from Vernonia oil, is transformed into 11-aminoundecanoic acid.

BACKGROUND OF THE INVENTION

Nylon-11 is an engineering resin used in various engineering plastics. Along with excellent dimensional stability, Nylon-11 exhibits excellent abrasion and vibration resistance. The Nylon-11 is used in electrical applications, e.g., cable extrusion, mechanical applications, e.g., to mold intricate components, and in the manufacture of sports equipment, industrial fabrics, powder coatings and synthetic fibers.

Presently, Castor oil is the precursor of 11-aminoundecanoic acid, the Nylon-11 monomer. However, the synthesis of Nylon-11 from Castor oil involves at least six reaction steps, including an energy intensive pyrolysis (450°–500° C.) reaction. In the present invention, 11-aminoundecanoic acid was produced through the intermediacy of 11-carbamoylundecanoic acid. There have been two reported syntheses of 11-carbamoylundecanoic acid. In U.K. Patent No. 1,283,796, 1,1'-peroxydicyclohexylamine was thermally decomposed below 450° C. to give decane-1,10-dicarbonimide, which was subsequently hydrolyzed to obtain the amide. Similarly, Kataoka and Ohno reported the synthesis of 11-carbamoylundecanoic acid from a cyclic-hydroxyimino ketone by treatment with concentrated sulfuric acid.

According to the present invention, Nylon-11 monomer is synthesized from 12-oxododecanoic acid oxime via the intermediacy of 11-carbamoylundecanoic acid and 11-(methoxycarbonylamino)undecanoic acid. U.S. Pat. Application Serial No. 08/065,333, provides for the synthesis of 12-oxododecanoic acid oxime from the seed oil of *Vernonia galamensis*, an annual herb, indigenous to tropical and sub-tropical Africa. The present invention provides a synthetic scheme in which one carbon atom is removed from the carbon backbone of the 12-oxododecanoic acid oxime. In the synthetic scheme of the present invention, the oxime is isomerized via Beckmann rearrangement to the amide (11-carbamoylundecanoic acid), which then undergoes Hofmann degradation and hydrolysis to give 11-aminoundecanoic acid.

SUMMARY OF THE INVENTION

According to the present invention, 12-oxododecanoic acid oxime is hydrolyzed in the presence of nickel acetate tetrahydrate to give 11-carbamoylundecanoic acid. The amide is then treated with a solution of sodium methoxide and bromine at 70°–80° C. to give 11-(methoxycarbonylamino)undecanoic acid at 75% yield, which upon hydrolysis and subsequent neutralization gives 11-aminoundecanoic acid.

This process of the present invention represents the first synthesis of Nylon-11 monomer from a compound that is derived from Vernonia oil, a renewable raw material. The process of the present invention is relatively simple and is performed under relatively mild conditions. The present invention offers an advantage over present process which uses Castor oil, including a reduction in the number of steps involved, and the elimination of an energy-intensive pyrolysis reaction. Additionally, the intermediate of the present process, 11-carbamoylundecanoic acid, may be a potential source of dodecane-1,12-diamine, one of the monomers of Nylon- 12,12.

DETAILED DESCRIPTION OF THE INVENTION

Figure 1:
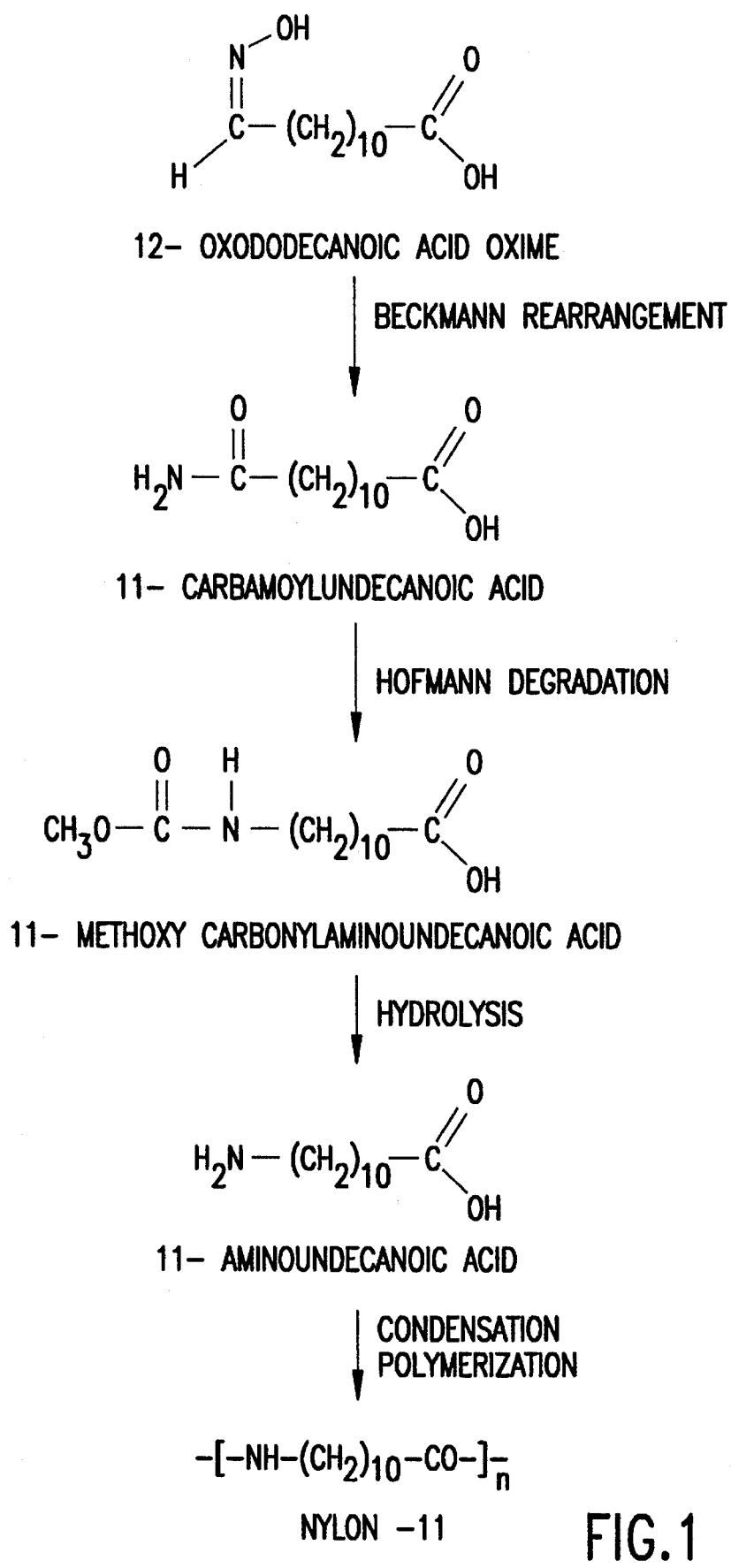
FIG. 1 shows the reaction scheme for the synthesis of 11-aminoundecanoic acid from 12-oxododecanoic acid oxime.

The synthetic sequence for the transformation of 12-oxododecanoic acid oxime to 11-aminoundecanoic acid is shown in FIG. 1. Several experimental trials were undertaken in each step in the sequence culminating in the present invention. A more complete description and understanding of the present invention is provided through a set of preferred steps for carrying out the present invention.

Isomerization of 12-oxododecanoic acid oxime to 11-carbamoylundecanoic acid

A 100 mL round-bottomed flask equipped with a magnetic stirring bar is charged with 5.00 g ($2.18 \times 10^{-2}$ mol) of 12-oxododecanoic acid oxime followed by the addition of 0.11 g ($4.41 \times 10^{-5}$ mol) of finely ground nickel acetate tetrahydrate, 0.5 mL of piperidine and 25 mL of p-xylene. For 24 hours, the resulting mixture is stirred continuously at 110°–115° C. The mixture is then cooled to room temperature with occasional stirring to facilitate crystallization of the solid product, which is filtered and rinsed with 15 mL of ice-cold hexane, resulting in a crude amide weighing 3.0 g (60% yield, mp. 124°–126° C.). Recrystallization in 20 mL ethanol/water mixture (4:1) gave 2.25 g of 11-carbamoylundecanoic acid (48% yield, mp. 129°–131° C., Lit. mp. 129°–130° C.).

Isomerization of the acid oxime to the amide is performed under neutral conditions since mineral acid catalysis of aldoximes results in the regeneration of the starting aldehyde. The rearrangement of the aldoxime to amide under conditions similar to those disclosed by Field, et al., *Journal of the American Chemical Society*, 83, 1983 (1961), in which the aldoxime was treated with catalytic amount of nickel acetate and refluxing in p-xylene for 5 hours, results in an incomplete reaction with only traces of the product being isolated. In fact, a tar-like reaction mixture left behind suggests the possibility of polymerization reactions. When the temperature for subsequent reactions is maintained at 110°–115° C., and reaction time is increased to 24 hours, the 48% yield of carbamoylondecanoic acid is realized.

Consequently, it is preferable for the reactions to be carried out at 110°–115° C. for 24 hours. The relatively low yield (48%) of the 11-carbamoylondecanoic acid is attributed to the aldoxime being a mixture of syn- and anti-isomers (ratio 7:3). An analysis of reaction mixture indicates that the anti-isomer is mostly unreacted, confirming reported studies indicating that Beckmann rearrangement reactions generally favor the isomerization of the syn-isomer. However, some studies have shown that boron triflouride in acetic acid converts both syn- and anti-isomers to amide in excellent yields, while other studies have demonstrated the ease of transforming aldoximes into the corresponding amides by using various transition metal catalysts.

Figure 2:
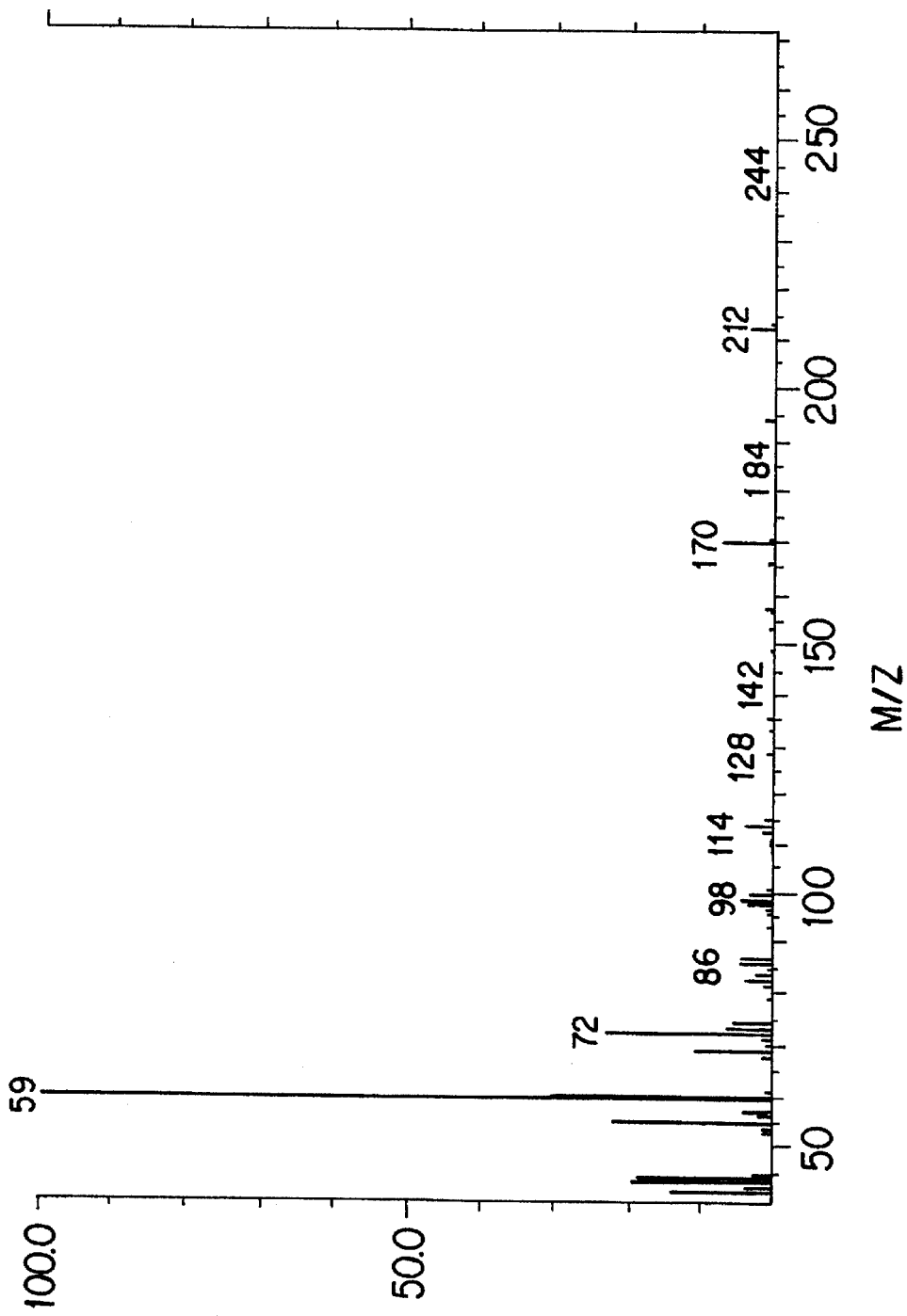
FIG. 2 is the mass spectrum of methyl 11-carbamoylundecanoate.

The mass spectrum of methyl 11-carbamoylundecanoate is shown in FIG. 2. The fragmentation pattern is that of a typical long chain aliphatic molecule. A weak M+1 ion is observed at m/z 244 and other diagnostic ions include: m/z 212 (M-OCH$_3$), 170 (M-CH$_2$CO$_2$CH$_3$) and 59 (Mclafferty-type rearrangement involving the carbamoyl group).

Figure 3:
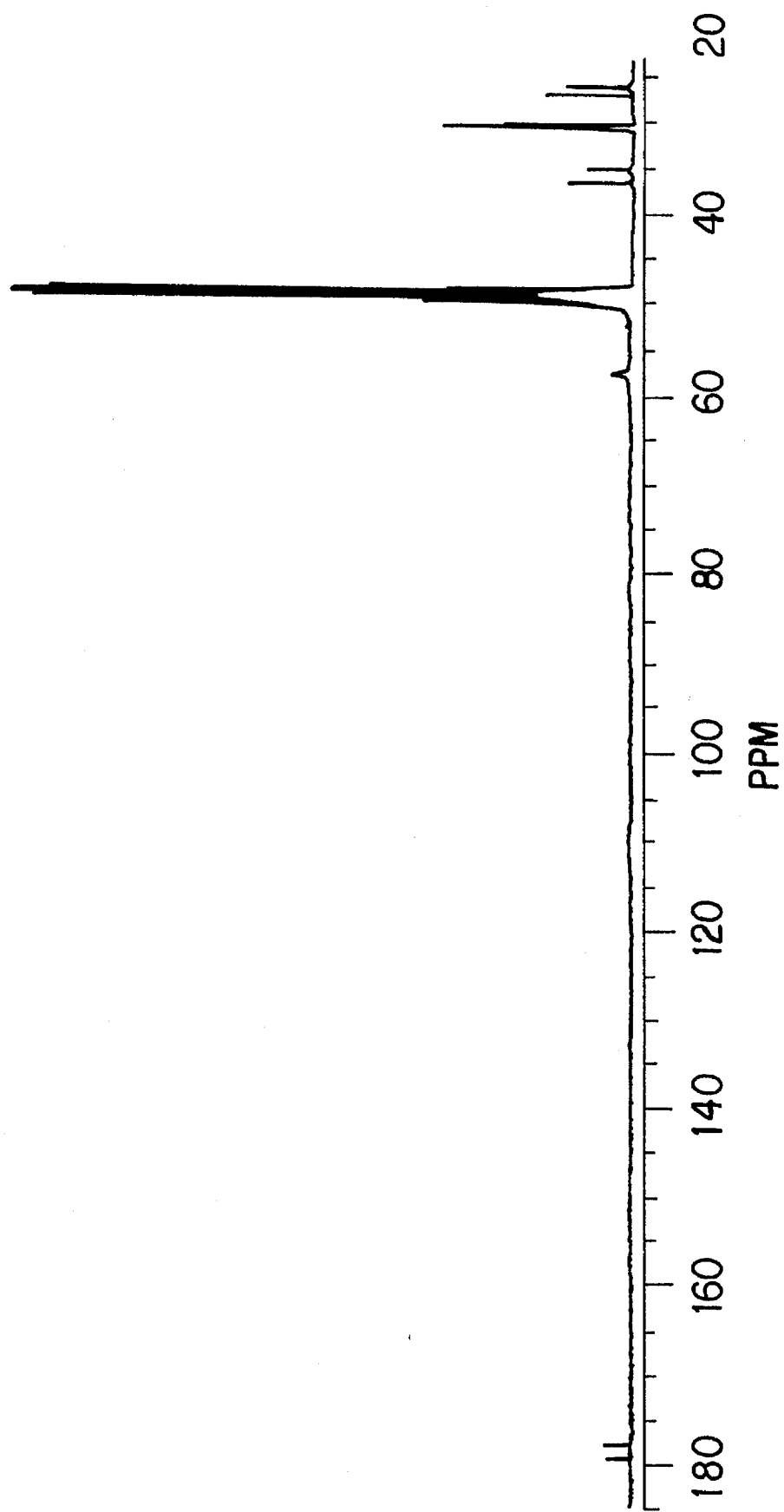
FIG. 3 is the carbon-nmr spectrum of 11-carbamoylundecanoic acid.
Figure 4:
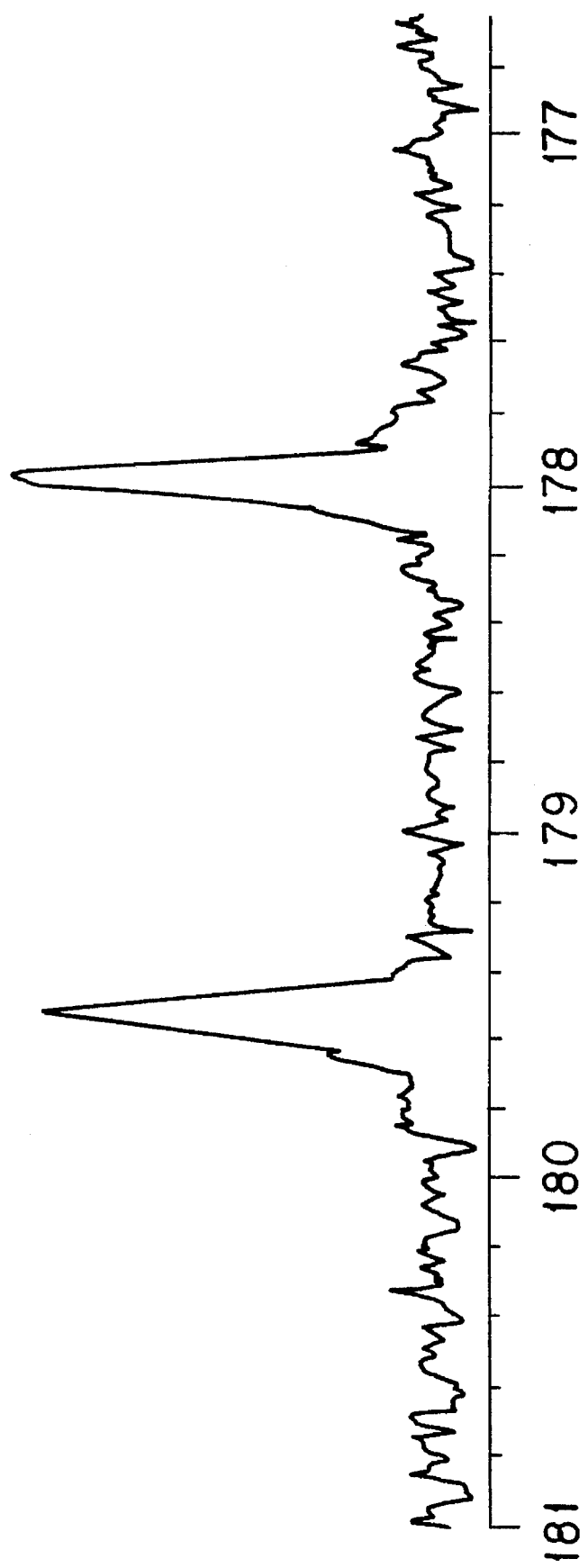
FIG. 4 is the carbonyl region of the carbon-nmr spectrum of 11-carbamoylundecanoic acid.

The infrared spectrum shows two fairly sharp peaks at 3450 cm$^{-1}$ and 3220 cm$^{-1}$ (N-H stretching bands). The O-H group stretching exhibit a characteristic absorption at 3200-2500 cm$^{-1}$ region. There are two C=O peaks at 1730 cm$^{-1}$ due to the carboxylic acid C=O and at 1650 due to the amide C=O. Other characteristic absorptions include N-H bending at 1600 cm$^{-1}$ and C-O stretching at 1460 cm$^{-1}$. The Carbon-13 nmr (FIGS. 3 and 4) indicated two carbonyl carbons absorption at 178.0 ppm (carbonyl carbon of amide) and at 179.5 ppm (carbonyl carbon of carboxylic acid).

Preparation of 11-(Methoxycarbonylamino)undecanoic acid (Methyl Carbamate)

Sodium methoxide in methanol is prepared by adding sodium 0.6 g (2.6×10$^{-2}$ mol) to 25 mL methanol in a 100 mL flask equipped with magnetic stirrer, condenser and addition funnel. (Alternatively, 11 ml 25 wt. % sodium methoxide/methanol (Aldrich Chemical Company, Inc., Milwaukee, Wis.) can be transferred to the 100-mL flask.) The solution is cooled with ice to approximately 5° C. Then a solution of 2.0 g (8.7×10$^{-3}$ mol) amide in 10 mL methanol is added to the cooled sodium methoxide solution. To the resulting solution 0.6 g (8.7×10$^{-3}$ mol) of bromine is added by mixing at 70°–80° C. in a water bath for 15 minutes. The flask is then cooled to 25° C., and the solution is made acidic (litmus paper) with acetic acid. Upon evaporation of the solvent, the resulting solid is washed with 50 mL water to remove sodium bromide and to yield a crude product weighing 2.03 g (89.8% yield). After recrystallization in 30 mL ethanol/water (1:1), 1.7 g methyl carbamate (75% yield, mp. 84°–86° C.; elemental analysis—Calculated for C$_{13}$H$_{25}$NO$_4$: C, 60.19; H, 9.73; N, 5.40; O, 24.68%,—found C, 60.02; H, 9.81; N, 5.26; O, 24.91% remains.

For the Hofmann degradation, the 11-carbamoylundecanoic acid is transformed to methyl carbamate by treating a solution of the amide in methanol with sodium methoxide and bromine. Several attempts at direct conversion of the amide to 11-aminoundecanoic acid by using concentrated sodium hydroxide solution and bromine resulted in the hydrolysis of the amide to give dodecanedioic acid in addition to some 11-aminoundecanoic acid.

Figure 5:
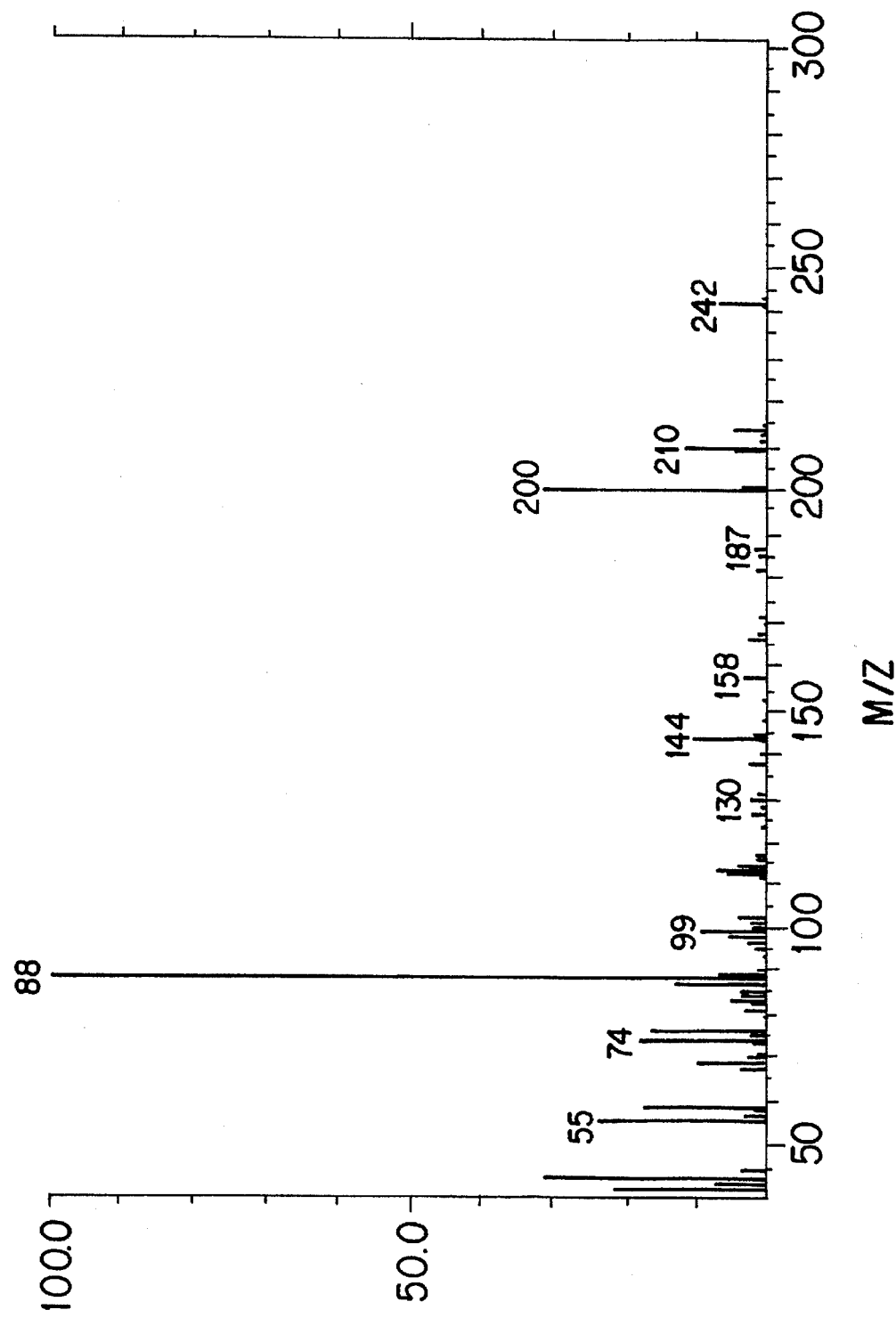
FIG. 5 is the mass spectral data of methyl 11-(methoxycarbonylamino)undecanoate.
Figure 6:
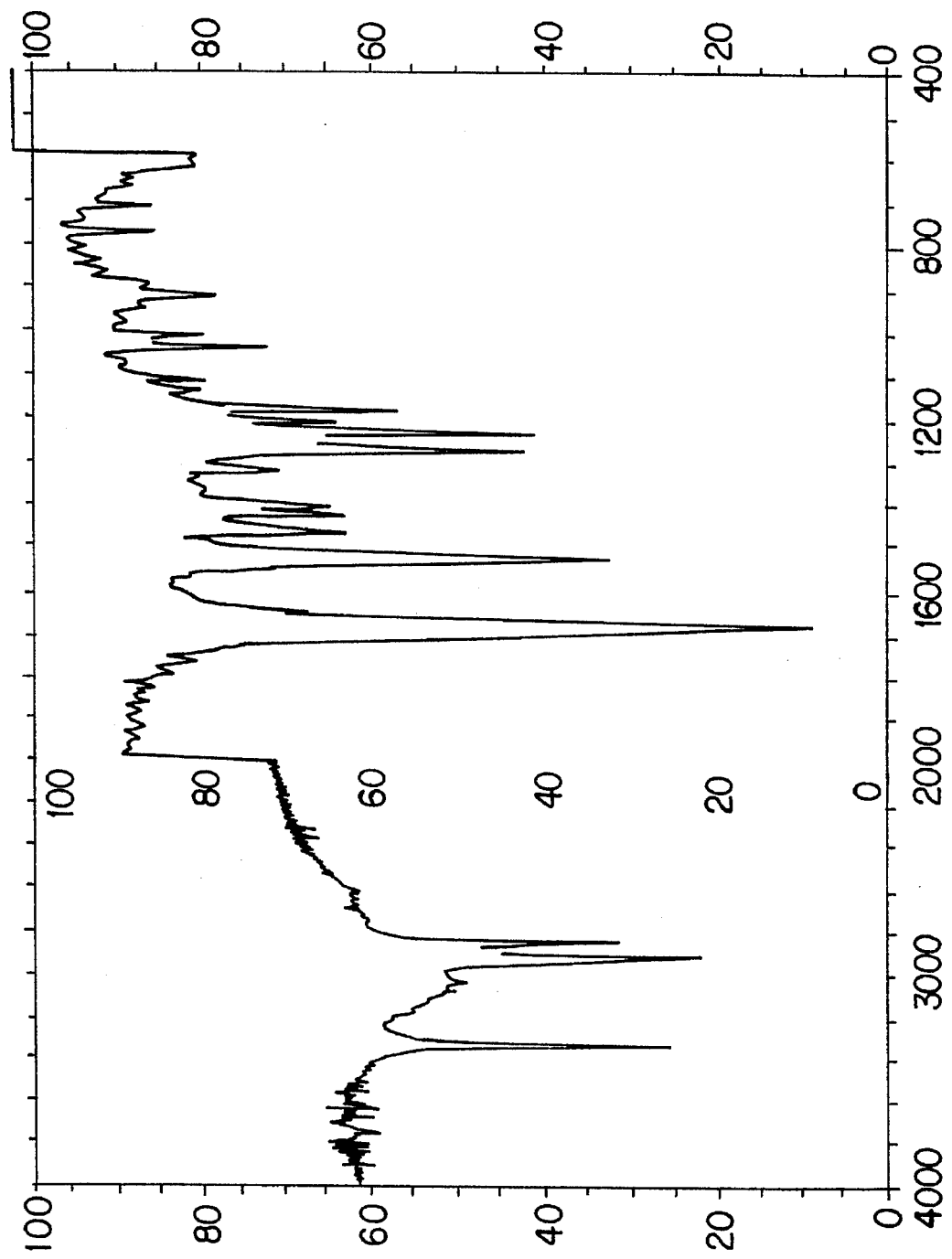
FIG. 6 is the infrared spectrum of 11-(methoxycarbonylamino)undecanoic acid.

The mass spectral data of methyl 11-(methoxycarbonylamino)undecanoate is shown in FIG. 5. The base peak at m/z 88 is attributed to cleavage of the C$_{10}$-C$_{11}$ bond. Other prominent diagnostic ions include: m/z 242 (M-OCH$_3$), 214 (M-carbomethoxy), 200 (M-73) and 144 [CH$_3$O$_2$CNH(CH$_2$)$_5$]$^+$. The infrared data (cm$^{-1}$) for 11-(methoxycarbonylamino)undecanoic acid, FIG. 6, shows a broad OH absorption at 3500-2500 cm$^{-1}$ which overlaps with a sharp absorption at 3370 due to N-H stretching vibration. Carbonyl absorption is shown at 1695, probably due to overlapping absorptions by the two carbonyl groups. C-N bending vibration gives an absorption at 1515 while C-N stretching appears at 1240 and 1280, and C-O stretching is observed at 1475.

Figure 7:
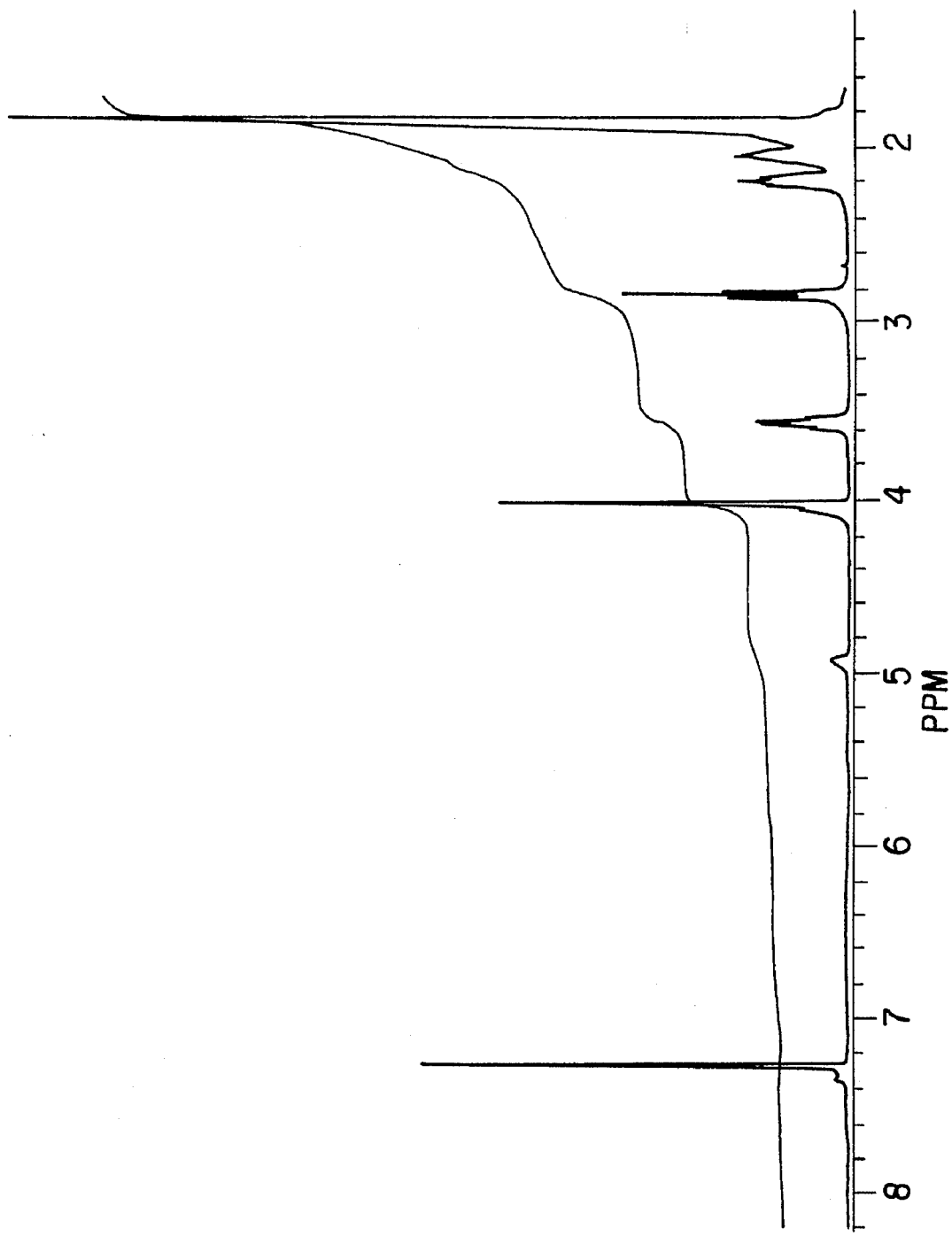
FIG. 7 is the proton-nmr spectrum of the methyl carbamate.
Figure 8:
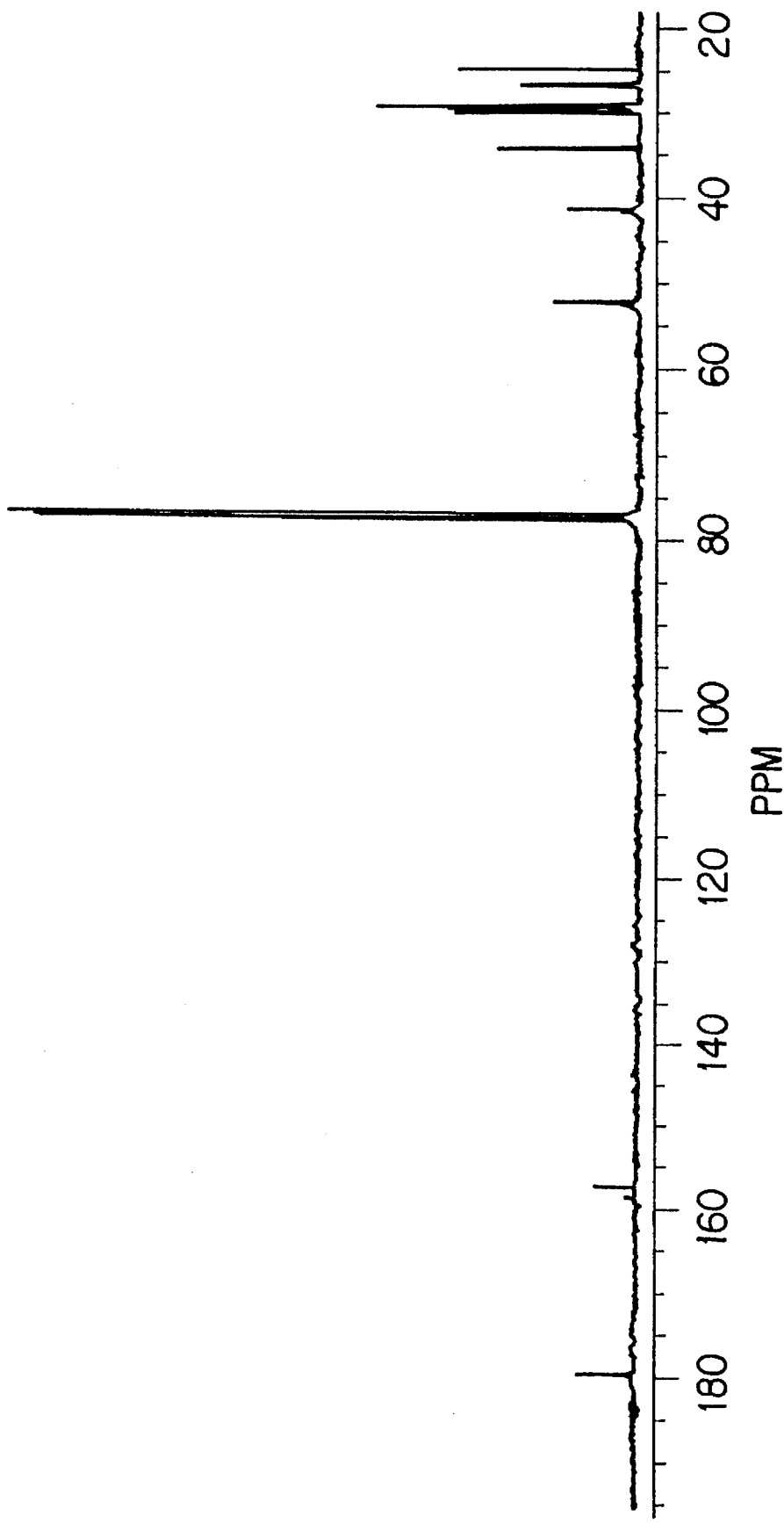
FIG. 8 is the Carbon-13 nmr spectrum of the methyl carbamate.

The proton-nmr spectrum of the methyl carbamate, FIG. 7, shows absorptions at 4.9 ppm (1H), 4.1 ppm (3H), 3.56 ppm (2H), 2.9 ppm (2H), 2.2 ppm (2H), 2.1 ppm (2H), 1.9 ppm (12H). The Carbon-13 nmr spectrum of the methyl carbamate, FIG. 8, shows two carbonyl signals, one at 179.37 ppm (attributed to the carbonyl carbon of the carboxylic acid) and one at 157.12 ppm (attributed to the carbonyl carbon of the carbamate). Other significant signals include the chemical shift at 55 ppm due to the methyl carbon, 42 ppm due to the methylene carbon alpha to the nitrogen and 35 ppm due to the methylene carbon alpha to the carboxylic acid group.

Hydrolysis of 11-(methoxycarbonylamino)undecanoic acid to 11-aminoundecanoic acid 1.0 g (3.9×10$^{-3}$ mol) of 11-(methoxycarbonylamino)undecanoic acid, is dissolved in 20 mL ethanol and added to 2.0 g (5.0×10$^{-2}$ mol) sodium hydroxide in 2 mL water. The mixture is refluxed for 17 hours, and the resulting gold-colored solution is cooled and neutralized with acetic acid to a pH of 7. The neutralized solution is filtered to remove any salt and the filtrate is stripped to yield crude amino acid. The crude acid is dissolved in 50 mL of water, cooled in ice and filtered to yield 0.41 g (53%). Recrystallizion from 16 mL ethanol/water (3:1) resulted in 0.26 g (34% yield) 11-aminoundecanoic acid (mp. 189°–192° C., Lit. mp. 190°–192° C).

Figure 9:
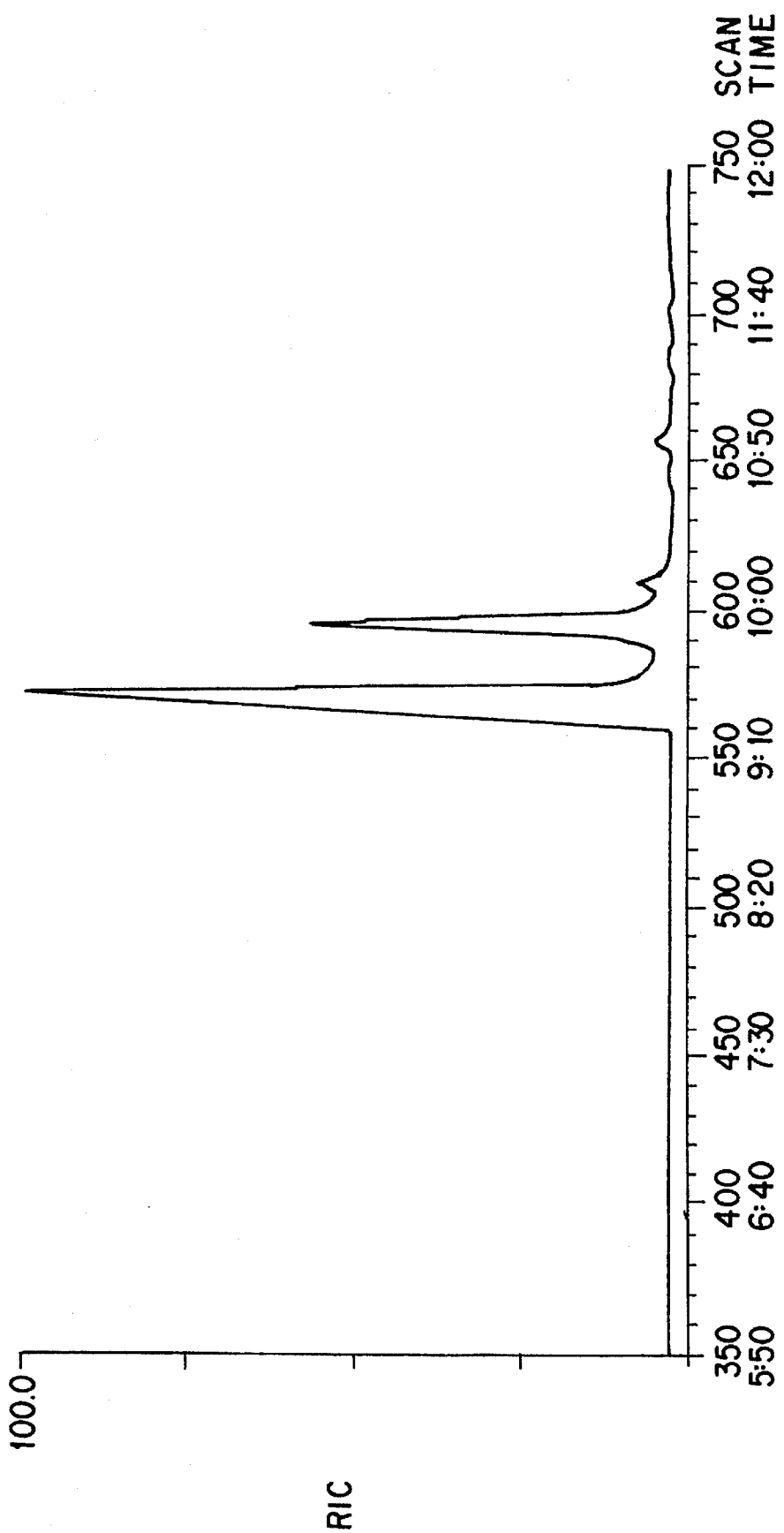
FIG. 9 is the gas chromatogram of the methylated sample of 11-aminoundecanoic acid.
Figure 10:
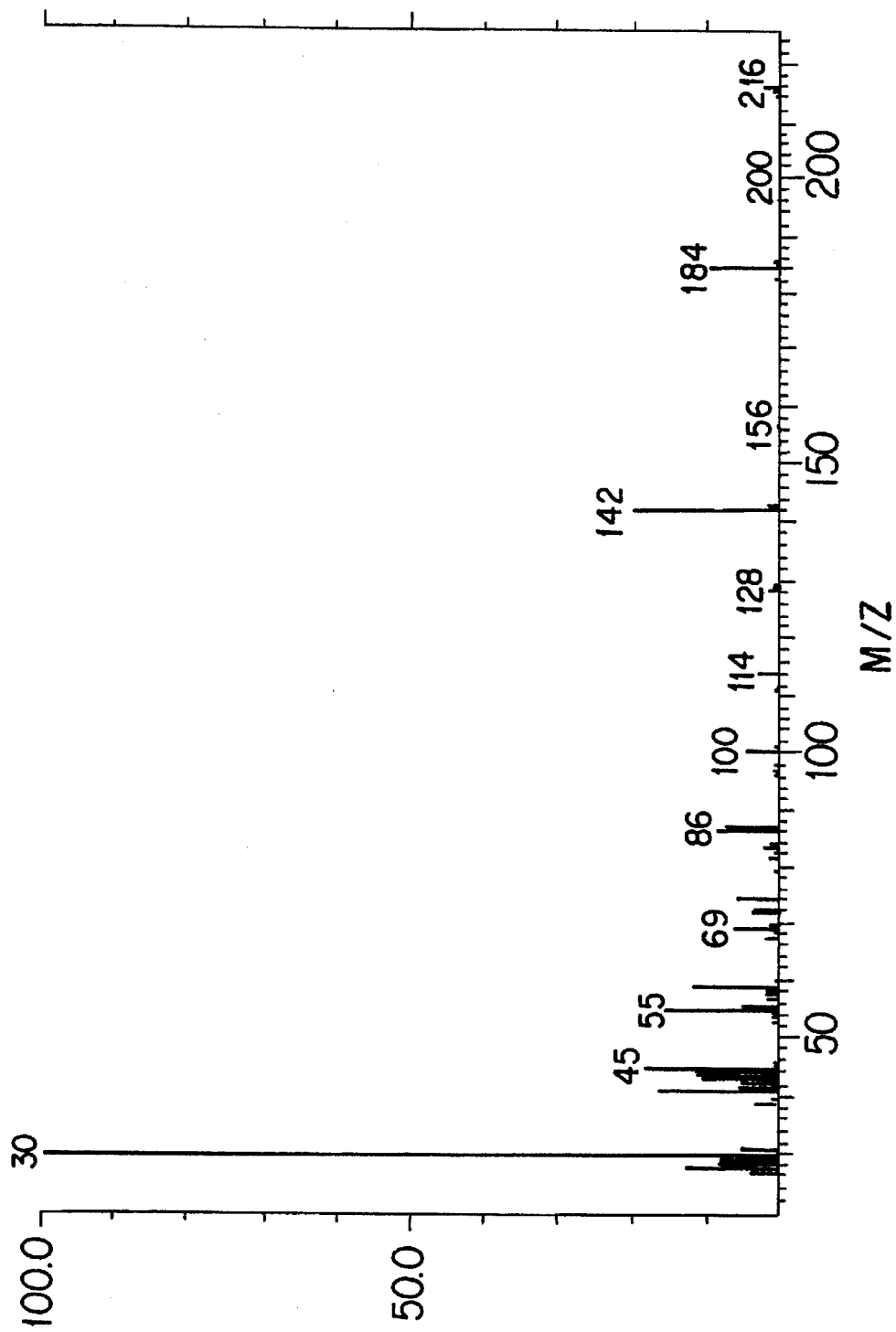
FIG. 10 is the mass spectrum of the primary amino ester.
Figure 11:
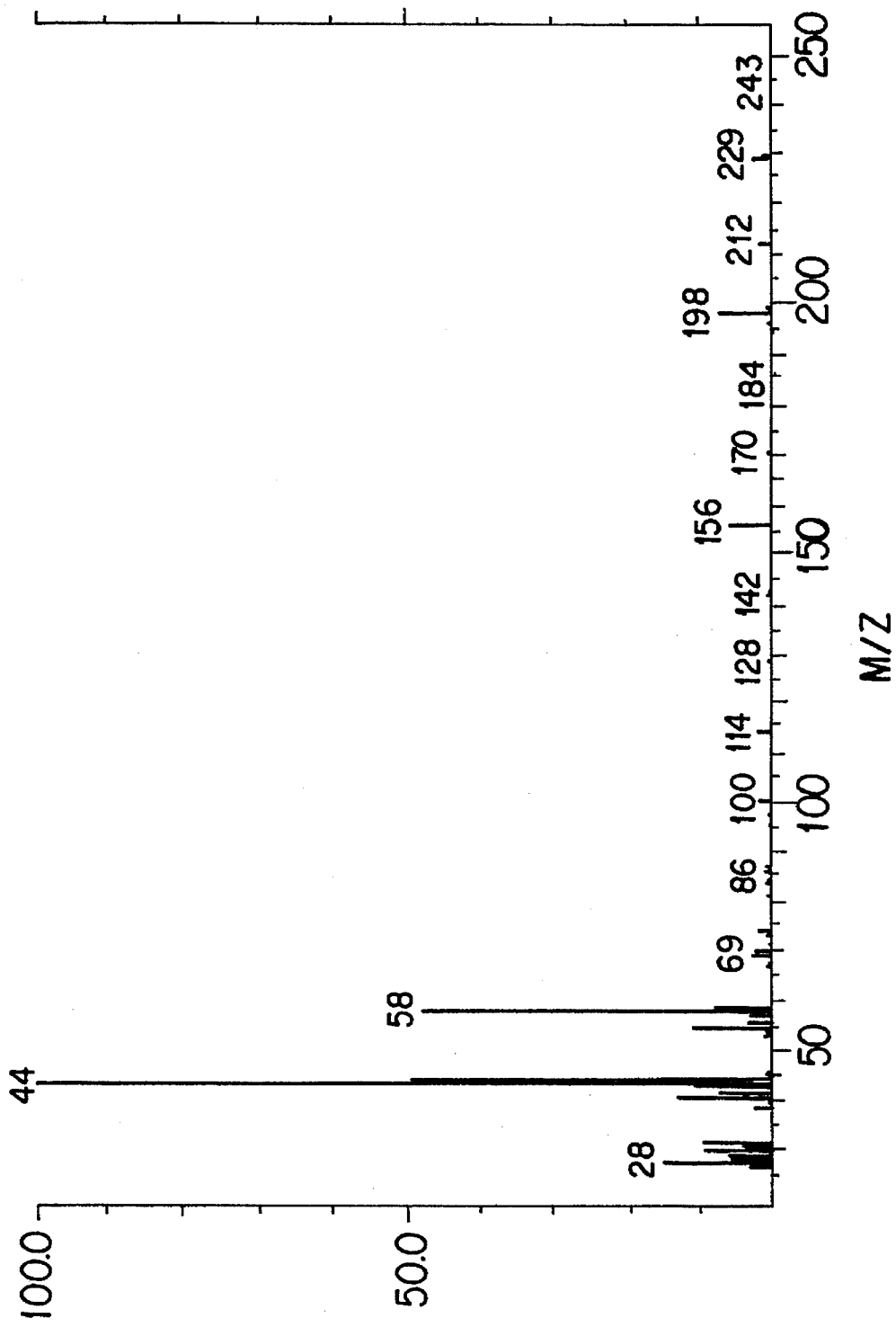
FIG. 11 is the mass spectral data of the tertiary amino ester.

Surprisingly, the hydrolysis of the methyl carbamate required a prolonged reflux of about 17 hours to give 53% yield of crude 11-aminoundecanoic acid, which was recrystallized in 16 mL ethanol/water (3:1) to obtain the 34% yield. The gas chromatogram of the methylated sample of 11-aminoundecanoic acid, FIG. 9, shows two peaks. Scan 570 corresponds to the primary amino ester H$_2$N(CH$_2$)$_{10}$CO$_2$CH$_3$ and Scan 595 corresponds to the tertiary amino ester (CH$_3$)$_2$N(CH$_2$)$_{10}$CO$_2$CH$_3$. Apparently, the amino group is methylated by diazomethane. FIG. 10 shows the mass spectrum of the primary amino ester with a protonated molecular ion (M+i) at m/z 216. Other fragmentation ions are m/z 184 (M-OCH$_3$), m/z 142 (M-CH$_2$CO$_2$CH$_3$) and m/z 30 (base peak). The mass spectral data of the tertiary amino ester, FIG. 11, gives a molecular ion (M+) peak m/z 243. Other prominent fragmentations include: m/z 212 (M-31), 58[(CH$_3$)$_2$NCH$_2$]$^+$, 86[(CH$_2$)$_2$NCH$_2$CH$_2$CH$_2$]$^+$ and 156 (M-CH$_2$CH$_2$CO$_2$CH$_3$).

The IR of 11-aminoundecanoic acid exhibits asymmetrical N-H stretching at 3400 cm$^{-1}$ and symmetrical N-H stretching at 3200 cm$^{-1}$. Almost overlapping these two bands are the strong OH absorption at 3300-2500 cm$^{-1}$. Also seen are C=O absorption at 1640 cm$^{-1}$, -NH$_2$ bending at 1540 cm$^{-1}$ and C-N stretching at 1400 cm$^{-1}$.

The potential commercial application of the synthetic scheme outlined in the above studies is enhanced by the fact that the 12-oxododecanoic acid oxime is derived from Vernonia Oil, a renewable raw material. The three-step reaction sequence to 11-aminoundecanoic acid is relatively simple and is performed under mild reaction conditions, offering an advantage over the current use of castor oil, which involves an energy-intensive pyrolysis reaction. Additionally, the 11-carbamoylundecanoic acid may be a potential source of dodecane-1,12-diamine, one of the monomers of nylon-12,12.

Consequently, we intend only to be limited by the following claims.

We claim:

1. A process for making 11-aminoundecanoic acid comprising:
   (a) a hydrolysis of 12-oxododecanoic acid oxime to form 11-carbamoylundecanoic acid; and
   (b) a Hofmann degradation of 11-carbamoylundecanoic acid.

2. A process for making 11-aminoundecanoic acid comprising:
   (a) a hydrolysis of 12-oxododecanoic acid oxime to form 11-carbamoylundecanoic acid;
   (b) a Hofmann degradation of 11-carbamoylundecanoic acid in an alcohol solvent; and
   (c) a hydrolysis of the reaction products of the Hofmann degradation.

3. A process for making 11-aminoundecanoic acid comprising:
   (a) a Hofmann degradation of 11-carbamoylundecanoic acid to form 11-(methoxycarbonylamino)undecanoic acid in an alcohol solvent; and
   (b) a hydrolysis of 11-(methoxycarbonylamino)undecanoic acid.

4. The process according to one of claims 1, 2 or 3, in which the alkyl ester of the acid is used in place of the acid.

* * * * *